United States Patent [19]

Rotsaert

[11] Patent Number: 4,970,032
[45] Date of Patent: Nov. 13, 1990

[54] PROCESSES FOR THE MANUFACTURE OF ARTIFICIAL TEETH AND CROWNS

[76] Inventor: Henri L. Rotsaert, 42 Brentwood Drive, Dundas, Ontario, Canada, L8T 3V8

[21] Appl. No.: 350,964

[22] Filed: May 12, 1989

[51] Int. Cl.⁵ ............... A61C 13/20; A61C 13/09; B32B 31/18
[52] U.S. Cl. ............... 264/20; 51/322; 264/139; 433/203.1
[58] Field of Search ............ 264/19, 20, 16, 138, 264/139; 433/202.1, 203.1, 212.1, 218, 223, 222.1; 156/153, 154; 51/322, 310, 311, 312

[56] References Cited

U.S. PATENT DOCUMENTS

| | | | |
|---|---|---|---|
| 2,514,076 | 7/1950 | Kelly | 264/20 |
| 3,126,429 | 3/1964 | Saffir | 264/20 |
| 3,423,829 | 1/1969 | Halpern | 264/20 |
| 4,433,959 | 2/1984 | Faunce | 433/222.1 |

Primary Examiner—Jan H. Silbaugh
Assistant Examiner—Christopher A. Fiorilla
Attorney, Agent, or Firm—Rogers & Scott

[57] ABSTRACT

A method for the manufacture of artificial teeth, either replacement whole teeth or crowns, whereby a tooth is produced by machining from a layered block of synthetic plastics materials, the layers being of predetermined varying color (hue), chroma, value and translucency to simulate the pulp, dentine and enamel layers in a real tooth, thereby providing an artificial tooth with the distribution and depth of color of a real tooth. The process provides for varying the tooth color by milling the tooth from a different section of the layered block to vary the thicknesses of the layers, at least at the labial, mesial, distal and occlusal surfaces, so as to obtain a custom tooth matched very closely to a patient's real tooth color and pattern. The process permits the manufacture of an artificial tooth from materials with a hardness closely matching that of a real tooth to provide similar wear properties.

8 Claims, 8 Drawing Sheets

PROCESSES FOR THE MANUFACTURE OF ARTIFICIAL TEETH AND CROWNS

FIELD OF THE INVENTION

This invention relates to a method for the manufacture of artificial teeth and crowns with colourings simulating as closely as possible those of real teeth.

BACKGROUND OF THE INVENTION

There are two main types of artificial teeth, namely crowns and denture teeth. Crowns are designed to fit a root stump which is left in the gum after the whole top part of the tooth has been removed, while denture teeth are intended to replace teeth which are no longer present. Denture teeth are usually attached to a bridge which extends between two teeth or to a plate which is worn against the upper or lower palate.

Crown teeth or crowns must be custom made because they must correspond at least approximately in shape to the teeth that they replace, and must fit whatever shape of stump is left for the attachment. Historically, crowns have been cast from a suitable metal which is left in its original colour, so that the contrast with the natural teeth make them quite obvious. A more cosmetically acceptable crown is moulded from ceramic material and then surface painted to match the surrounding teeth as closely as possible. Such crowns and the process by which they are made have a number of disadvantages. For example the process is very labour intensive and the painted-on colour wears off in time. In addition, the ceramic materials from which these crowns are made are harder than natural teeth and this often results in accelerated wear of the opposing teeth. Finally, even with careful workmanship it is difficult to make the appearance of a painted tooth match that of the adjacent real teeth. Teeth are made up of three major layers, namely an interior pulp, a surrounding dentine, and an outer coating of enamel; the enamel and dentine are translucent so that all three layers contribute to the colour which is visible from outside the tooth. The resulting depth and distribution of colour in a natural tooth is very difficult to duplicate.

A new crown making technology which has recently become available provides a tooth body made from synthetic material, usually platic material, which is shaped in a computer-controlled milling machine and then surface painted. The process is highly automated and provides great savings in labour, while another benefit is that the hardness of these teeth can be matched more closely to that of natural teeth. The problems of surface wear of the painted-on colour and the less natural look of a painted-on surface are still present.

Denture teeth generally are not custom made, but instead are provided in a wide assortment of standard shapes, sizes and colours, from which the denture maker may choose. At one time most denture teeth were moulded from homogeneous blocks of ceramic and surface painted in a manner similar to that described above for crown tooth manufacture. Current technology provides denture teeth which are moulded with a number of internal successive coloured layers, each of the layers contributing to the colour which is visible on the outside of the tooth. This moulding process provides a tooth with a depth and distribution of colour more closely resembling that of a natural tooth, but requires at least three separate moulds for each tooth and would be prohibitivly expensive in a custom process for producing individual crowns.

DEFINITION OF THE INVENTION

It is an object of the invention to provide new methods for custom manufacturing crowns and artificial teeth with colour as close as possible to a natural tooth.

It is another object to provide an artificial tooth comprising a number of successive internal coloured layers to simulate as closely as possible the colouring of a natural tooth.

According to the present invention there is provided a method of manufacturing an artificial tooth of a required colour comprising:

providing a blank including a core portion having lingual, labial, mesial, distal, gingival and occlusal sides, the core portion approximating in shape at least at its labial, mesial and distal sides to the shape of a corresponding core portion of the tooth to be manufactured therefrom;

reference means on the blank establishing a reference point from which the removal of material from the blank can be determined;

and at least one layer of another material or materials overlaying at least the occlusial, labial, mesial and distal surfaces of the core portion; and selectively removing material from the block to form the tooth and expose at least at the labial, mesial and distal sides the said at least one layer of said another material in a thickness or thicknesses to provide a tooth shaped artificial tooth of the required colour at least at the labial, mesial and distal surfaces thereof.

Also in accordance with the invention there is provided a blank for the manufacture of an artificial tooth of a desired colour comprising:

a core portion having lingual, labial, mesial, distal gingival and occlusal sides, the core portion approximating in shape at least at its labial, mesial and distal sides to the shape of a corresponding core portion of a tooth to be manufactured therefrom by removal of material from the blank;

reference means on the blank establishing a reference point from which the removal of material from the blank can be determined;

and at least one layer of another material or materials overlaying at least the occlusial, labial, mesial and distal surfaces of the core portion;

the core portion and the at least one other layer together providing at least the labial, mesial and distal surfaces the required colour for the tooth upon selective removal of material from the block to leave a tooth-shaped artificial tooth.

DESCRIPTION OF THE DRAWINGS

Particular perferred embodiments of the invention will now be descirbed, by way of example, with reference to the accompanying diagrammatic drawings; wherein.

DESCRIPTION OF THE PREFERRED EMBODIMENTS

The method of the invention preferably makes use of a commercially available system which was developed by La Société Hennson in France for milling teeth from a homogeneous block of plastics material which has the desired milling and wear characteristics. With this system the patient's teeth are examined to determine the size and shape of the tooth or crown required, the surrounding and opposing teeth being also measured to ensure a correct replacement, these measurements being obtained with an endoscope mounted laser camera. The colouring of the surrounding teeth must also be determined so as to be able to make the new tooth match the existing tooth colour as closely as possible. The measured parameters obtained from this examination are input into a computer control system which will guide the milling machine to develop the required tooth shape and colour, as will be described below.

Figure 1:
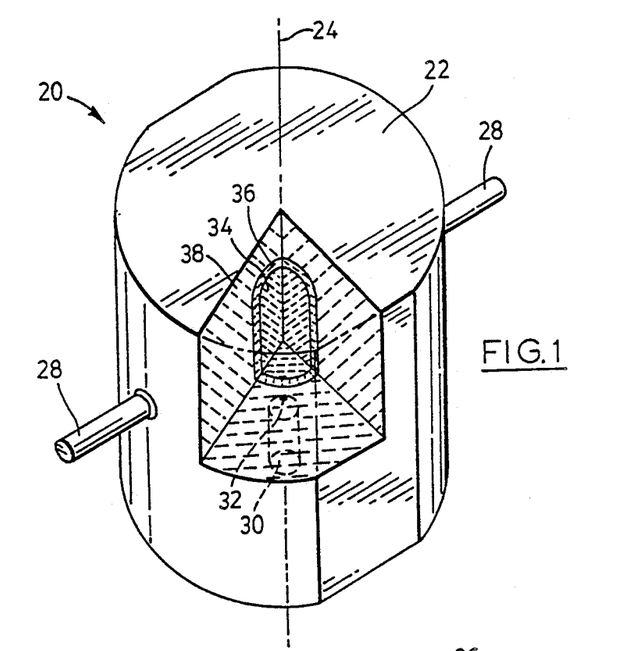
FIG. 1 is a perspective view of the exterior of a layered block from which an artificial tooth can be produced by milling, part of the block being cut away to reveal the internal layering.
Figure 2:
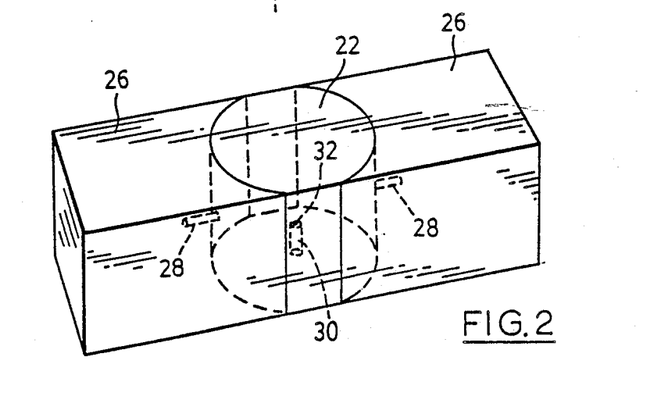
FIG. 2 is a perspective view of a tooth blank, comprising a layered block as in FIG. 1, which is used in the production of an artificial tooth.

The method employs a blank 20 as shown in FIG. 1 comprising a central portion 22 of standard shape, which in this embodiment is cylindrical with the cylindrical axis 24 extending occlusially-gingivally. This central portion is provided at its mesial and distal sides with two standard shaped wing portions 26 to form a complete blank as shown in FIG. 2, these wing portions constituting means by which the block is held in the milling machine for removal of material therefrom. The central portion is provided with mesially, distally extending protrusions 28 about which the wings are moulded, as by injection moulding. The central portion is also provided with an occlusially-gingivally extending bore 30 through which the axis 24 passes, the junction of this axis and the bottom surface of the bore constituting a reference point 32 to which all meansurements of the milling machine can be referred to ensure the accuracy of the milling operation.

The central portion 22 is shown in FIG. 1 as having a segment cut away to show its interior, and it will be seen that there is a central core portion 34 which approximates in shape, at least at its labial, mesial and distal sides, to the shape of a corresponding core portion of the particulare tooth to be manufactured from the blank by removal of material using the computer controlled milling machine. In this particular embodiment the tooth is one of the lower incisors. This central portion is overlaid, at least at its occlusial, labial, mesial and distal surfaces by a relatively thin first layer 36 of another material of different colour to the core material. The layer 36 is in turn overlaid by a second layer 38 of another material of a different colour from the other two materials, this second layer being made sufficiently thick that it forms the desired cylindrical shape of the central portion 22. Such a blank is readily made by injection-moulding the core and the layers in successive operations.

Figure 3:
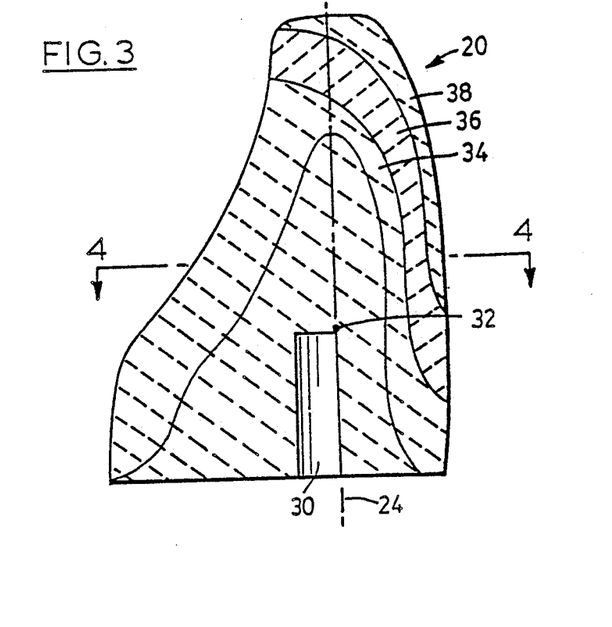
FIG. 3 is a cross-sectional view in an occlusial-gingival extending plane of an inscisor tooth showing a preferred arrangement of the successive coloured layers in the manufactured tooth.
Figure 4:
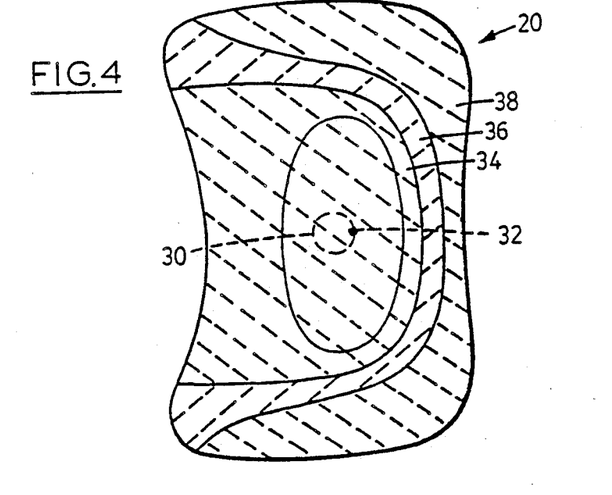
FIG. 4 is a cross-sectional view of the tooth of FIG. 3 in a mesial-distal plane, taken on the line 4—4 in FIG. 3.

The blank is mounted in the milling machine and the tooth shape is now milled therefrom so as to provide at the occlusical, labial, mesial and distal surfaces of the core portion 34 the thicknesses of the layers 36 and 38 such that with their colour and translucency the resulatent incisor tooth will have as closely as possible the desired colour to match the adjoining teeth, without the need to paint colour on the external surface, as in the prior art methods. The cross-section through such a tooth, taken in the occlusal-gingeval extending plane is shown in FIG. 3, while the corresponding mesial-distal cross-section is shown in FIG. 4. It will be seen that the gingeval and lingual surfaces of the tooth are constituted by the material of the shoulder or central core portion 34, so that there is no control of the colour of these two surfaces, but this is immaterial since the gingival surface abuts the tooth stump to which the crown is fastened, and the lingual surface is only seen by someone inspecting the interior of the mouth, such as the prosthodontist.

The blank preferably is made by injection moulding the different coloured materials one on the other from suitable plastics materials such as acrylics, polyurethanes, dimelthylacrylates, and composites thereof. All three materials of the different layers can be of the same chemical composition, with the exception of the inclusion therein of different fillers to provide the different colours and translucency that are required to provide a suitable range of tooth colours from a single blank. It will usually be necessary to provide a number of different blanks for the full range of replacement teeth that must be provided, owing to differences in size, basic colour and colour distribution. Since the central core portion 34 approximates the basic shape of the tooth to be manufactured, it will be seen that different blanks will also be required for the other tooth shapes present in the human mouth, namely the canines, bicuspids and molars, both upper and lower.

Figure 5:
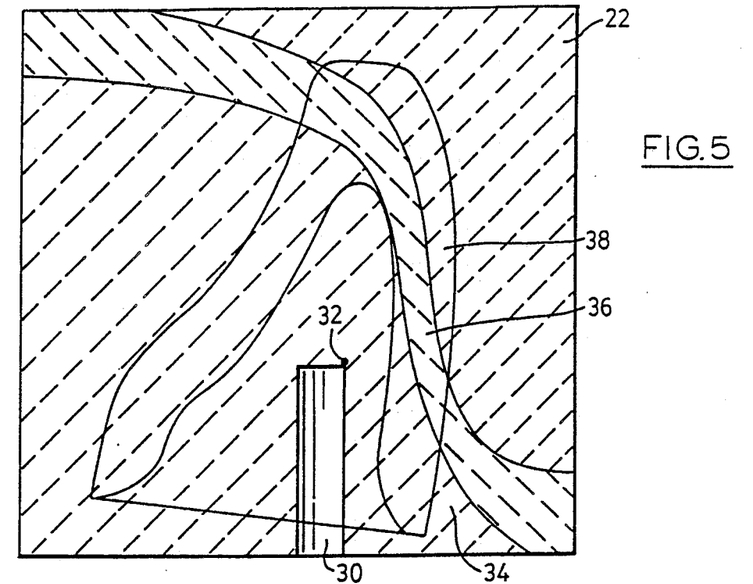
FIG. 5, 6 and 7 are cross-sections taken in the same plane as FIG. 3 showing the arrangment of layers in the layered block as seen in this plane, and with different outlines of an incisal tooth, as seen from the mesial or distal direction, superimposed on different portions of the layered block to provide different arrangments of layers and thereby provide different colourings for the tooth.
Figure 6:
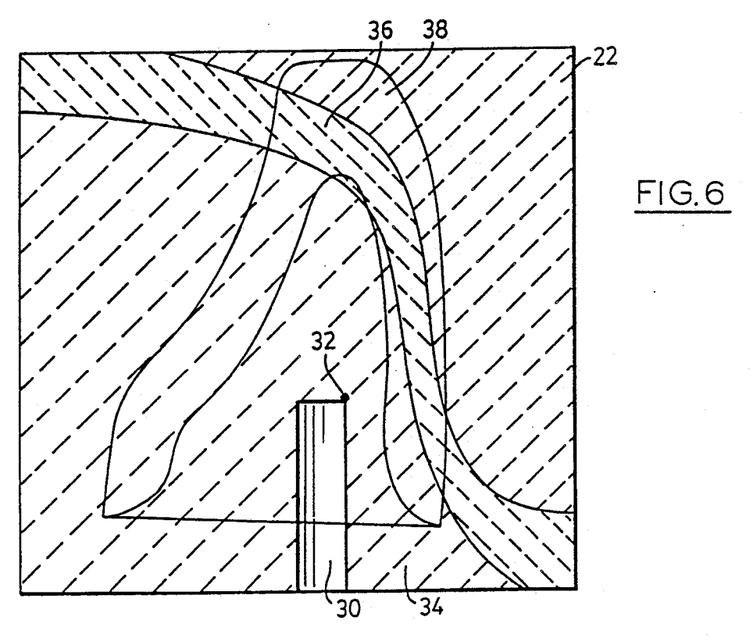
Figure 7:
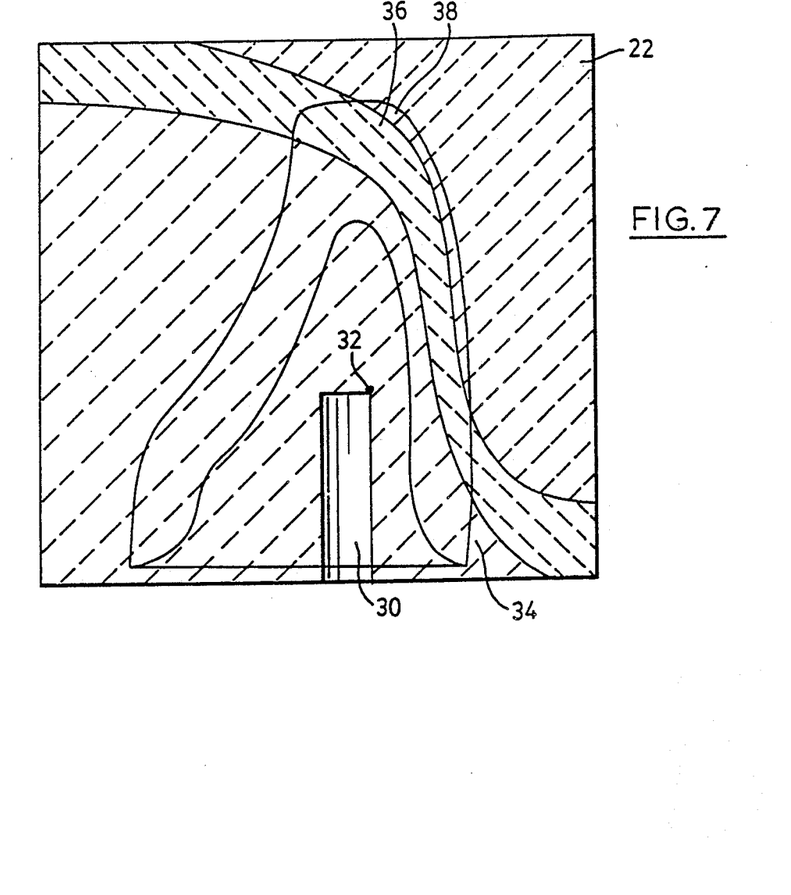

FIGS. 5, 6 and 7 illustrate the manner in which different tooth colours and colour distributions can be achieved from the same basic shoulder or core portion 34 and layers 36 and 38. Thus, in the tooth of FIG. 5 the profile is tilted toward the labial and extends close to the gingival surface, so that the layer 38 is relatively thick at the incisal occlusal surface and the upper part of the labial surface, while the gingival portion of the labial surface is provided by the layers 6 and the core 34. The profile in FIGS. 6 and 7 is more upright and are respectively closer to the occlusal and gingival surfaces, thereby correspondingly varying the thicknesses and thickness distribution of the layers 36 and 38 and the resultant tooth colour and colour distribution. It will be seen therefore that in these particular embodiments the three material layers 34, 36 and 38 can be regarded as corresponding respectively approximately to the pulp, dentine and enamel (incisal material) of the human tooth and their thicknesses and transparency or translucency, particularly of the two layers 36 and 38, can be adjusted to give the equivalent colour (hue) and colour density or saturation (chroma) of the tooth which is replaced by the artificial tooth. As the outer layer is thinner, then the colour and translucency of the underlying layers contributes more to the colour of the tooth as seen by the observer, as with the pulp, dentine and enamel of natural teeth. The hardness of the material is of course chosen to approximate as closely as possible that of the human tooth it replaces, so that its wear characteristic will be similar to that of the adjacent teeth, and its characteristic change of colour with age and wear will also be similar.

Figure 8:
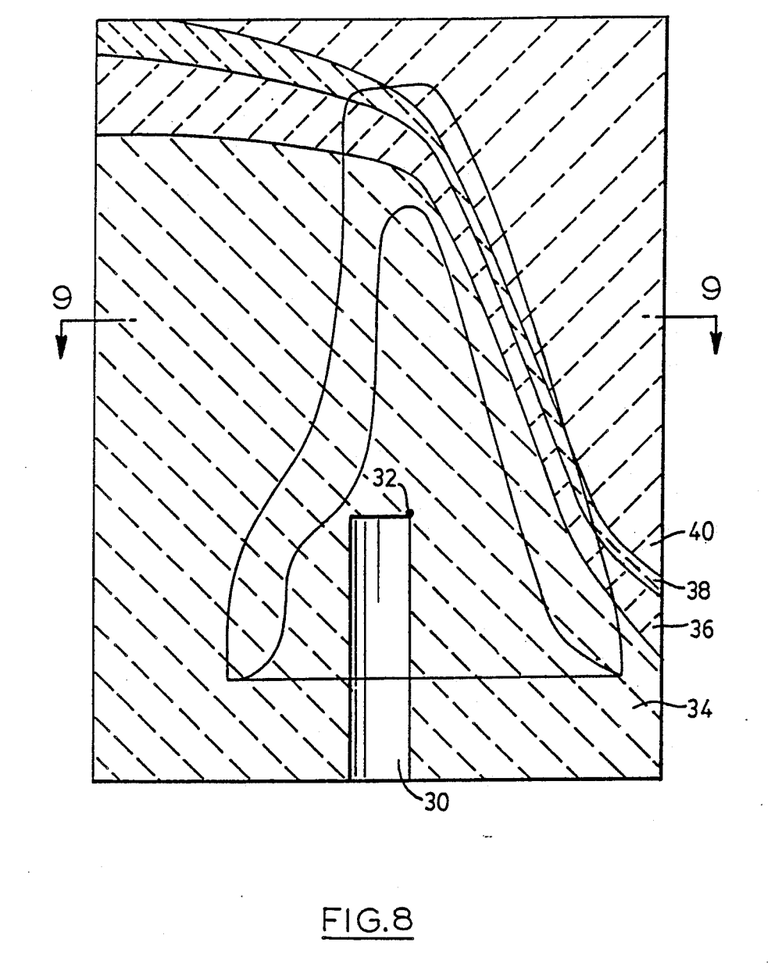
FIGS. 8 and 9 are views similar to FIGS. 3 and 4 respectively of a different embodiment employing an additional intermediate layer.
Figure 9:
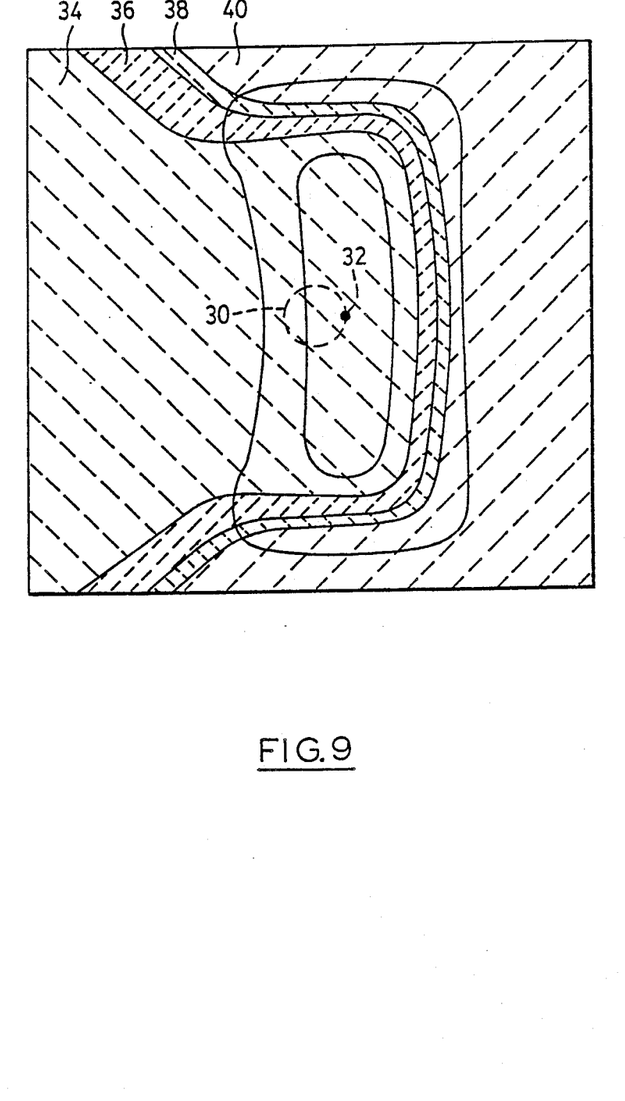

FIGS. 8 through 11 show a further development of the invention in which the core 34 is provided, at least overlying its occlusal, labial, mesial and distal surfaces, with three superimposed layers 36, 38 and 40, the last layer 40 being the layer that is extended to form the block of standard external size, which with these embodiments can be rectangular in plan and elevation. FIG. 8 shows a mesial-distal view of the tooth in an occlusal-gingival plane and it will be seen that the lingual surface is almost entirely within the core 34, except close to the occlusal end. The occlusal incisal surface is provided by the two layers 38 and 40, while the labial surface starts occlusially with the outer layer 40 and crosses the layers 38 and 36 to terminate at its gingival end in the core material 34. FIG. 9 is an occlusal view of FIG. 8 taken on the line 9—9 in FIG. 8.

Figure 10:
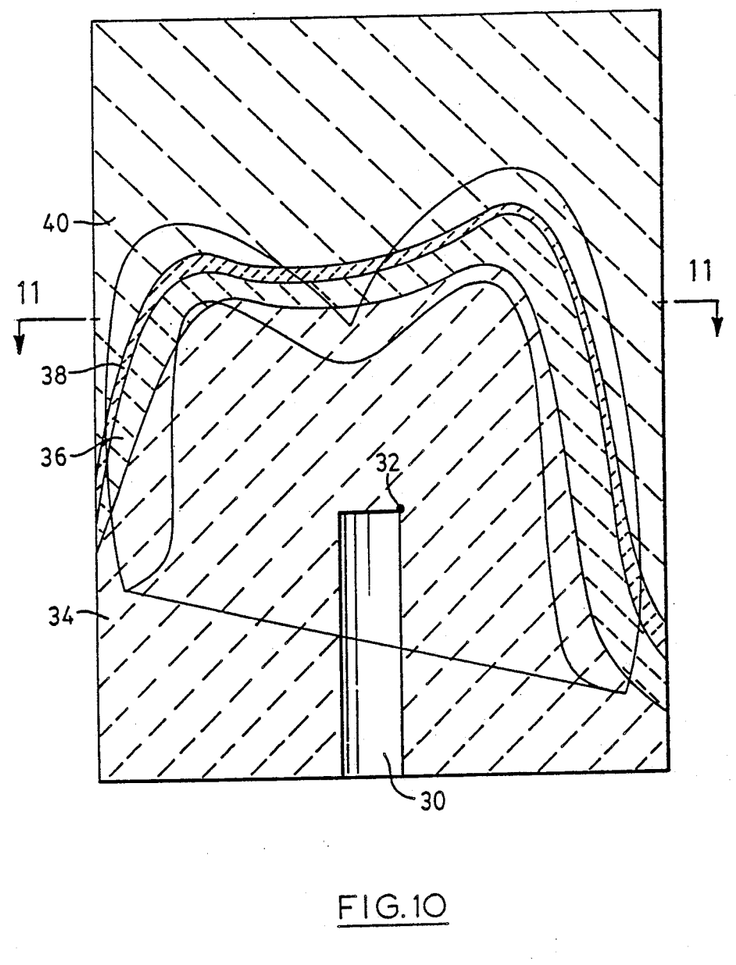
FIGS. 10 and 11 are views similar to FIGS. 8 and 9 respectively and showing the block in conjunction with the outline of a bicuspid tooth superimposed thereon.
Figure 11:
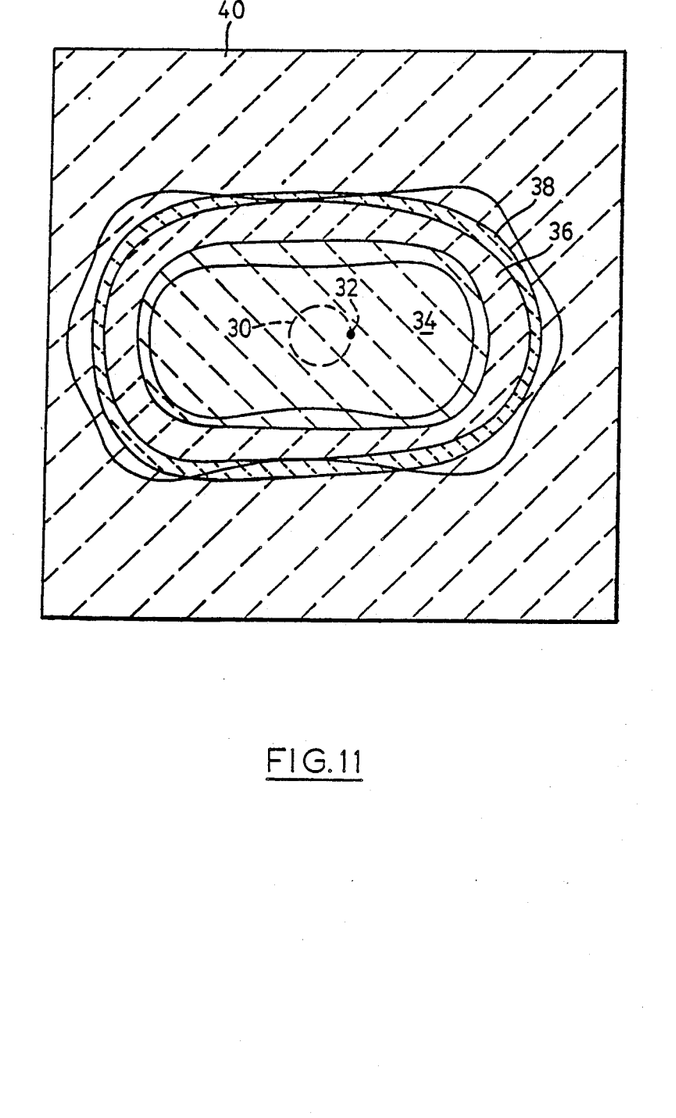

FIG. 10 is a similar cross section to FIG. 8 of a block intended for the production of a bicuspid tooth crown and showing the profile thereof, while FIG. 11 is an occlusal view taken on the line 11—11 in FIG. 10.

Although the invention has so far been described in its application to the production of replacement crowns, it is equally applicable to the production of replacement denture teeth, when each tooth will be provided with a suitable root portion to facilitate its mounting in the supporting plate or bridge.

The provision of four layers provides even greater flexibility in obtaining the desired tooth colour and colour distribution. The colour is sometimes in the industry referred to as the hue, while the value is the gray scale value for a particular colour. The colour density or saturation is referred to as the chroma. There are a number of systems already employed in the industry to characterize tooth colour for replacement teeth and crowns, such as the Lumin Vac Shade Guide of Vita G.m.b.H, to which reference can be made.

The core material 34 can have its own distinctive colour since it will frequently appear at least at the gingival end of the labial surface, or it can be given the desired dentine or base colour. The first layer 36 can instead or in addition be given the base or dentine colour, while the second layer 38 can be an intermediate dentine colour to give the desired wider variation. The third layer 40 simulates the incisal material and is coloured appropriately, or in some embodiments can be completely clear, particularly with blanks for the production of anterior teeth.

In a particular preferred embodiment intended for the manufacture of an incisal tooth, as illustrated by FIG. 8 the block 22 may measure about 9 cm in the mesial-distal direction, and about 1.2 cm in both the occlusal-gingival and labial-lingual directions. The replacement tooth for an upper central incisor typically measures about 9.5 mm occlusially-gingivally, about 1.5 mm labially-lingually at the occlusal surface, about 6.5 mm labially-lingually at the gingival surface, and about 8 mm mesially-distally. In such an embodiment the first layer 36 may have a thickness of about 0.3 mm at the labial surface increasing progressively at the occlusal surface to about 0.75 mm, and also increasing progressively at the gingival end to about the same. The second layer 36 may have a thickness of about 0.2 mm at the labial surface increasing progressively to about 0.5 mm at the occlusal and gingival ends.

I claim:

1. A method of manufacturing an artificial tooth of a required color comprising:

providing a blank including a core portion having lingual, labial, mesial, distal, gingival and occlusal sides, the core portion approximating in shape at least at its labial, mesial and distal sides to the shape of a corresponding core portion of the tooth to be manufactured therefrom;

reference means on the blank establishing a reference point from which the removal of material from the blank can be determined;

and at least one layer of another material or materials overlaying at least the occlusial, labial, mesial and distal surfaces of the core portion; and selectively removing material from the block to form the tooth and expose at least at the labial, mesial and distal sides the said at least one layer of said another material in a thickness or thicknesses to provide a tooth shaped artificial tooth of the required color at least at the labial, mesial and distal surfaces thereof.

2. A method as claimed in claim 1, wherein the at least one other layer of another material or materials comprises a first layer of a respective material overlaying the core portion and a second layer of a respective material overlaying the first layer, the material of the first layer simulating the dentine of a tooth and the material of the second layer simulating the incisal material of a tooth.

3. A method as claimed in claim 1, wherein the at least one other layer of another material comprises a first layer of a respective material overlying the core portion, a second layer of a respective material overlying the first layer, and a third layer of a respective material overlying the second layer, the material of the first layer simulating the dentine of a tooth and the material of the third layer simulating the incisal material of a tooth.

4. A method as claimed in claim 1, wherein the materials of all of the layers are of the same chemical composition and differ from one another only in their colour.

5. A method as claimed in claim 1, wherein the outermost layer is of a shape to form a block of standard external size and shape irrespective of the sizes and shapes of the first core portion and the said at least one other layer.

6. A method as claimed in claim 1, wherein the reference means for the blank is a bore within the core portion opening to its gingival side, the reference point being at the bottom of the bore within the core portion.

7. A method an claimed in claim 1, wherein the blank includes on its mesial and distal sides two standard shaped wing portions constituting means by which the block is held in a machine for removal of material from the blank.

8. A method as claimed in claim 1, wherein the first core portion and the at least one another layer are formed by injection moulding from plastic material.

* * * * *